United States Patent [19]

Jones et al.

[11] Patent Number: 4,878,382

[45] Date of Patent: Nov. 7, 1989

[54] METHOD OF MONITORING THE DRILLING OPERATIONS BY ANALYZING THE CIRCULATING DRILLING MUD

[75] Inventors: Timothy G. J. Jones, Cottenham; Trevor L. Hughes, Cherry Hinton, both of England

[73] Assignee: Schlumberger Technology Corporation, Houston, Tex.

[21] Appl. No.: 263,499

[22] Filed: Oct. 27, 1988

[30] Foreign Application Priority Data

Nov. 14, 1987 [GB] United Kingdom ............... 8726727

[51] Int. Cl.$^4$ .............................................. E21B 47/00
[52] U.S. Cl. ................................... 73/153; 73/61 R; 175/40
[58] Field of Search ............... 73/53, 61 R, 61.4, 151, 73/153; 175/40, 66; 436/29, 30

[56] References Cited

U.S. PATENT DOCUMENTS

| | | | |
|---|---|---|---|
| 3,433,312 | 3/1969 | Burdyn et al. | 175/66 |
| 3,512,164 | 5/1970 | Bynum | 73/153 |
| 3,802,259 | 4/1974 | Eckels | 73/153 |
| 4,369,665 | 1/1983 | Scearce | 73/153 |

OTHER PUBLICATIONS

Mills, "Continuous Determination . . . Drilling Mud Helpful", The Oil Weekly, Aug. 1, 1938.

Primary Examiner—Michael J. Tokar
Assistant Examiner—Kevin D. O'Shea
Attorney, Agent, or Firm—Stephen L. Borst

[57] ABSTRACT

Samples of mud are taken periodically at the surface at one or several locations where the mud does not contain cuttings anymore. The mud samples are analyzed on the rig site to determine the successive values, as a function of time or depth, of a parameter representative of the weight of the fine solids present in the mud. In one aspect of the invention the weight of the fine solids present in the mud is determined by measuring the weight of the liquid phase of the mud and the weight of the electrolyte dissolved in a known weight of mud. Preferably the weight of the liquid phase is determined by drying to constant weight a given weight of mud and the weight of electrolyte is determined by chemical analysis of the mud filtrate using an ion chromatography system on the rig site.

11 Claims, 4 Drawing Sheets

METHOD OF MONITORING THE DRILLING OPERATIONS BY ANALYZING THE CIRCULATING DRILLING MUD

This invention relates to a method of monitoring the drilling operations and more particularly, the drilling fluid, called drilling mud, to identify changes in the drilling process by monitoring continuously a parameter representative of the weight of fine solids present in the mud.

In the rotary drilling of wells, such as hydrocarbon wells, a mud is continuously circulated from the surface down to the bottom of the hole being drilled and back to the surface again. The mud has several functions, one of them being to transport the cuttings drilled by the drill bit up to the surface where they are separated from the mud. Another function is to impose an hydrostatic pressure on the walls of the borehole so as to avoid a collapse of the borehole and a surge of gas or liquid present into the formations being drilled. The characteristics of the mud are therefore important to monitor and to keep within certain limits. For example, the density must be large enough so as to exert a certain hydrostatic pressure on the formations but not too large to fracture these formations. The viscosity of the mud is also an important characteristic since it contributes to the cutting transport capability of the mud. Weighting materials, barite for example, are added to the mud to make it exert as much pressure as needed to contain the formation pressures. Clay is added to the mud so as to keep the bit cuttings in suspension as they move up the hole. The clay also sheathes the wall of the hole. This thin layer of clay, called wall cake, makes the hole stable so it will not cave in or slough. Numerous chemicals are available to give the mud the exact properties it needs to make it as easy as possible to drill the hole.

Maintaining the stability of the borehole is one of the major problems encountered in drilling oil and gas wells. Hole instability is evidenced by the squeezing of soft, ductile formations into the borehole, the excavation under stress of hard, brittle formations and the caving of shales with consequent hole enlargement. These problems increase drilling time and thus cost and may result in stuck drill pipe.

The various forms of hole instability resulting from the interaction between the drilling fluid and the subterranean formations penetrated by the borehole are related to the hydration and dispersion of the clay sediments.

The current practice on the drilling rigs is to make a number of measurements on the mud system, usually at a rate of one per day, the main object of which is to monitor the efficiency of the solids control equipment in removing fine drilled solids from the mud. These measurements are not interpreted in terms of lithology or mud-formation interactions, but are used for maintaining the solids content of the mud within certain bounds for the purposes of controlling rheology, mud weight, quality of filter cake and drilling rate. The emphasis of the measurements is therefore to keep the mud to some specification of performance.

On the other hand, a test, called in the industry the methylene blue test, is currently used to measure the cation exchange capacity (CEC) of the mud solids to quantify bentonite in the mud. The determination of bentonite in the mud is the only use made of this test.

The present invention is directed to a method of monitoring the drilling operations by analysing the circulating drilling mud. Samples of mud are taken periodically at the surface at one or several locations where the mud does not contain cuttings anymore. The mud samples are analyzed on the rig site to determine the successive values, as a function of time or depth, of a parameter representative of the weight of the fine solids present in the mud.

In one aspect of the invention the weight of the fine solids present in the mud is determined by measuring the weight of the liquid phase of the mud and the weight of the electrolyte dissolved in a known weight of mud.

Preferably the weight of the liquid phase is determined by drying to constant weight a given weight of mud and the weight of electrolyte is determined by chemical analysis of the mud filtrate using an ion chromatography system on the rig site.

In a more specific aspect of the invention, the fractional weight solids content of the mud is determined for each sample.

A specific embodiment of the invention will now be described by way of example with reference to the accompanying drawing in which.

Figure 1:
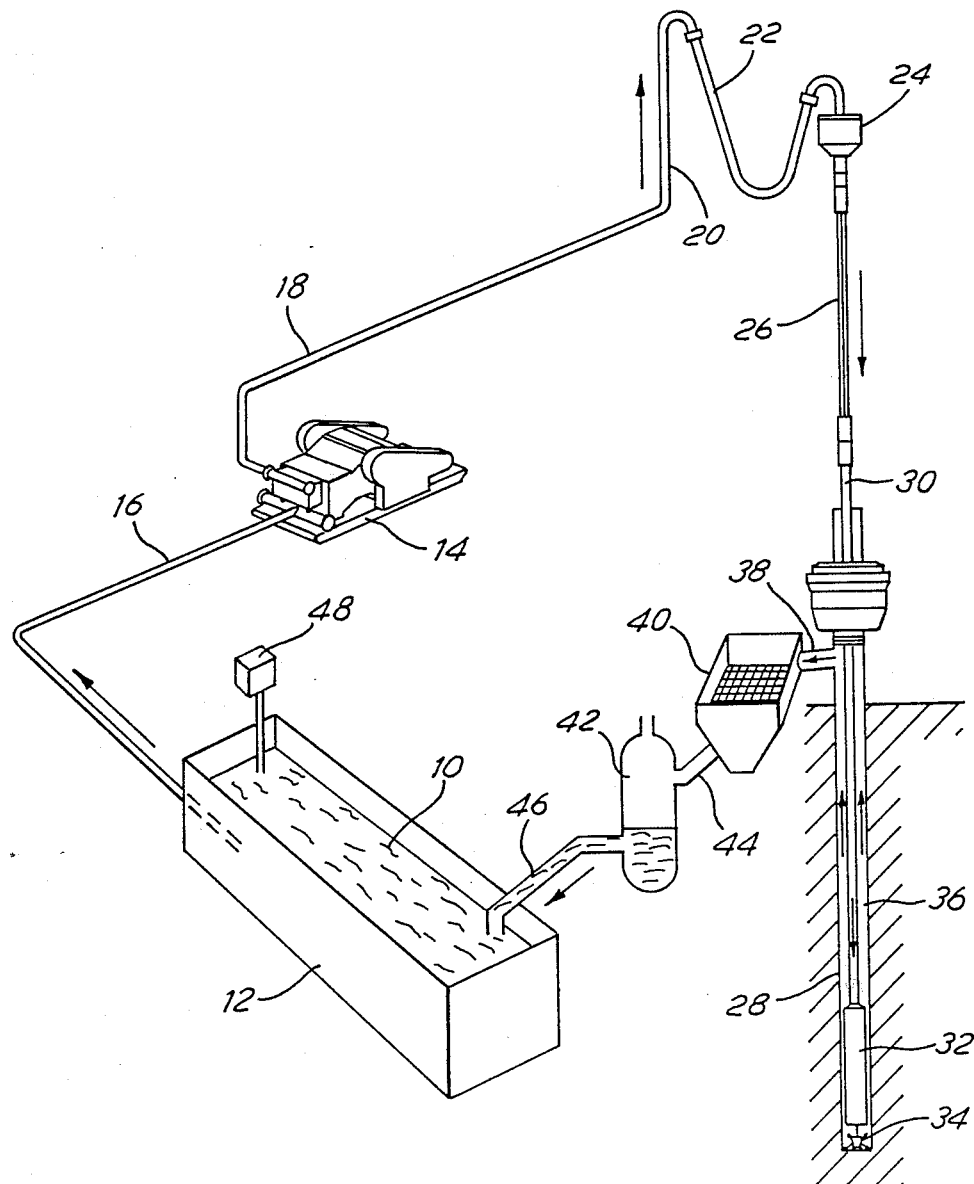
FIG. 1 shows schematically the circulating system of the mud used in the oil rigs.

Referring to FIG. 1, which shows the mud circulation equipment, the mud 10 is contained in a mud pit 12, called the active tank. A pump 14 draws up the mud from the pit through a pipe 16 and forces the mud through the discharge line 18, the stand pipe 20, the rotary hose 22 and the swivel 24. The mud then flows into the kelly 26 and down the borehole 28 in the drill pipe 30 and the drill collars 32. The mud reaches the bottom of the hole at the drill bit 34 and then flows up the surface in the annulus 36 and in the mud return line 38. The mud then falls over a vibrating screen-like device 40, called a shale shaker. The role of the shale shaker is to separate from the liquid phase of the mud, the cuttings drilled by the bit 34 and transported up in the annulus by the mud. The separation is made by having the mud passing through a screen which vibrates. The solids which are larger than the mesh size of the screen don't pass through the screen and are rejected either in a reserve pit when the drilling rig is on land or in a barge when the drilling operations are conducted offshore. The solid particles contained in the mud which have a size smaller than the mesh size of the screen pass through the screen and therefore remain in the mud. These fine solids comprise part of the weighting material added to the mud to reach a certain mud density and also fine solids from the formations traversed by the borehole. After the shale shaker 40, the mud flows into a solid control equipment, represented schematically by 42, through the pipe 44. The solid control equipment 42 could include a degasser, a desilter and a desander. Then the mud falls into the pit 10 through the pipe 46. A mud-mixing hopper 48 is generally used to add solid materials like clay and barite to the mud in the active tank.

The following description of the invention refers to experiments which have been made with mud samples taken from both the active tank 12 and from the pipe 44 between the shale shaker 40 and the solids control equipment 42. For each sample, the weight percent solids content of the mud was measured. The measurements were used to give the quantitative determination of solids removal by the solids control equipment, the effect of mud dilution operations, the build-up of fine drilled solids and the correlation of solids content to the drilled lithology.

The fractional weight solids content W of mud is defined by $$w = \frac{M_s}{M_m}, \quad [1]$$

where $M_s$ is the weight of solid in a weight $M_m$ of mud. The weight of mud can be decomposed into the weight of solid $M_s$, liquid phase $M_l$ (which could be water and/or oil) and electrolyte $M_e$ dissolved in the liquid $$M_m = M_s + M_l + M_e \quad [2]$$

and thus $$w = \frac{M_m - M_l - M_e}{M_m} \quad [3]$$

The mass $M_e$ of electrolyte in the aqueous phase of the mud is due to the total dissolved solids (TDS). In terms of the volume fraction $v_s$ of solids in the mud $$w = \frac{V_s d_s}{V_m d_m} = v_s \frac{d_s}{d_m} \quad [4]$$

where $d_m$ and $d_s$ is the density of the mud and the mud solids, respectively.

The determination of w involves measurement of the weight $M_w$ and $M_l$ of liquid and electrolyte in a weight $M_m$ of mud. A given weight of mud is dried to constant weight using drying apparatus such as a small oven or an infra-red drying balance. The weight loss on drying is the weight of liquid $M_l$. When the liquid is water, the drying temperature must be at least 105° C. to ensure that the water in the mud solution phase is removed. The weight of the dried solids contains a weight $M_e$ of solid electrolyte which must be subtracted.

The weight of electrolyte $M_e$ in the liquid phase is given by $$M_e = \frac{TDS \cdot M_l}{1000 \cdot d_l} \quad [5]$$

where TDS is the total weight of electrolyte in the mud in grams per liter and $d_l$ is the density of the liquid (in g.cm$^{-3}$). The total dissolved solids is determined by $$TDS = \Sigma_i c_i M_i^m \quad [6]$$

wherein $c_i$ is the concentration and $M_i^m$ the molar mass of ion i. The concentration $c_i$ of ion i is determined by the chemical analysis of the mud filtrate at the rig site, preferably using an ion chromatography system such as described in our copending UK patent application No. 8705502.

A sample calculation is given using data from a suite of field mud samples which are presented thereafter, the liquid phase being water:
weight of mud sample, $M_m = 3.841$ g
weight loss on drying, $M_l = 2.704$ g
total dissolved solids, TDS = 49.3 g/l
from equation [5], weight of electrolyte, $M_e = 0.133$ g
from equation [2], weight of mud solids, $M_s = 1.004$ g
from equation [3], fractional weight mud solids, $w = 0.261$ It should be noted that the correction for the weight of electrolyte $M_e$ is significant. If the weight $M_e$ of electrolyte in the mud sample is neglected, then the apparent solids content rises to 0.296 which is a difference of 13.4%. Clearly the saltier the mud, the greater the error if $M_e$ is ignored. An accurate measurement of w should therefore be accompanied by the determination of TDS. The accuracy of the solids content measurements is 0.1%.

Figure 2:
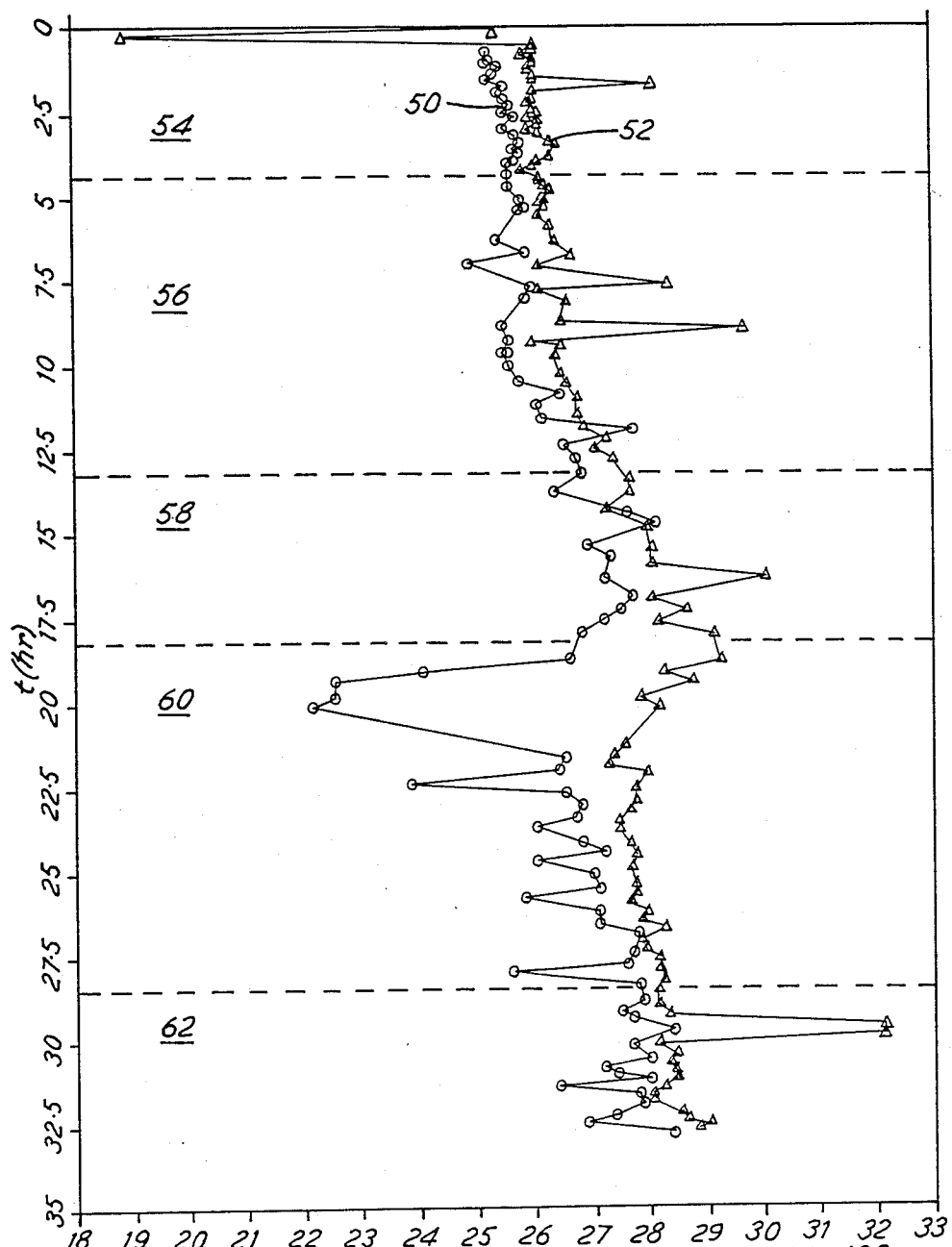
FIG. 2 is a plot of the weight percent solids content versus the sample time for a section of a well which has been drilled.

FIG. 2 shows the variation of the weight percent solids content (ie, w $\times$ 100) of a suite of field mud samples. The mud was sampled in two different locations: the round points 50 correspond to samples taken from the active tank 12, while the triangle-shape points 52 correspond to samples taken immediately below the shaker 40 in the return mud pipe 44, before the solids control equipment 42. Superimposed on FIG. 2 is the drilled lithology converted to sample time t (in hours) from a knowledge of the drilled depth as a function of time and the annulus lag time (calculated to be in the range 50-60 minutes over this drilled section). The five formations are marl 54, limestone 56 and three distinct shale units 58, 60, and 62. The horizontal dotted lines represent the formation boundaries.

Figure 3:
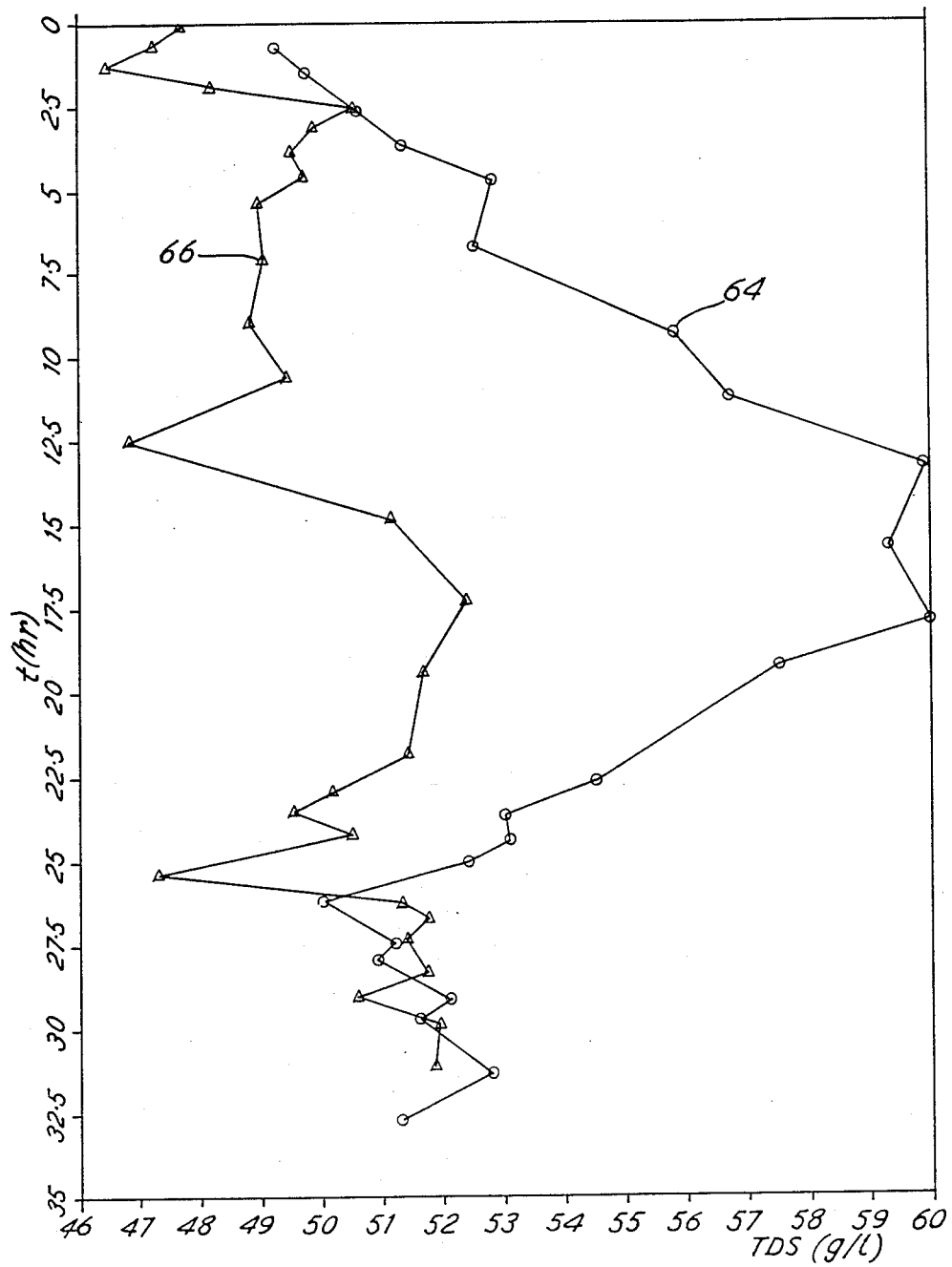
FIG. 3 is a plot showing the weight percent solids content versus the sample time, for values respectively corrected and uncorrected for the total dissolved solids in the mud.

FIG. 3 shows the dependence of the total dissolved solids (TDS), in g/l, of the mud samples on the sample time t (in hours). The TDS data shown in FIG. 3 have a rounded shape 64 for the samples taken from the active tank 12 and a triangle shape 66 for the samples taken between the shale shaker and the solids control equipment 42. These data were used in equations [3] and [5] to calculate w. The mud samples on which the TDS was measured account for only about a quarter of the number shown in fig 2; the value of TDS for the remaining samples was obtained by interpolation. The TDS is generally larger in the active tank samples and therefore failure to correct for $M_e$ leads to greater error in the active tank solids content than in the return mud samples.

It is believed that larger TDS values for the active tank samples compared with the return line samples are due to solids added in the mud in the tank, such as sodium hydroxide, which were not homogeneously dispersed in the tank and their concentration was larger at the location the samples were taken. This suggests that it is probably more appropriate to sample the mud at a location between the discharge line 18 and the kelly 26.

Figure 4:
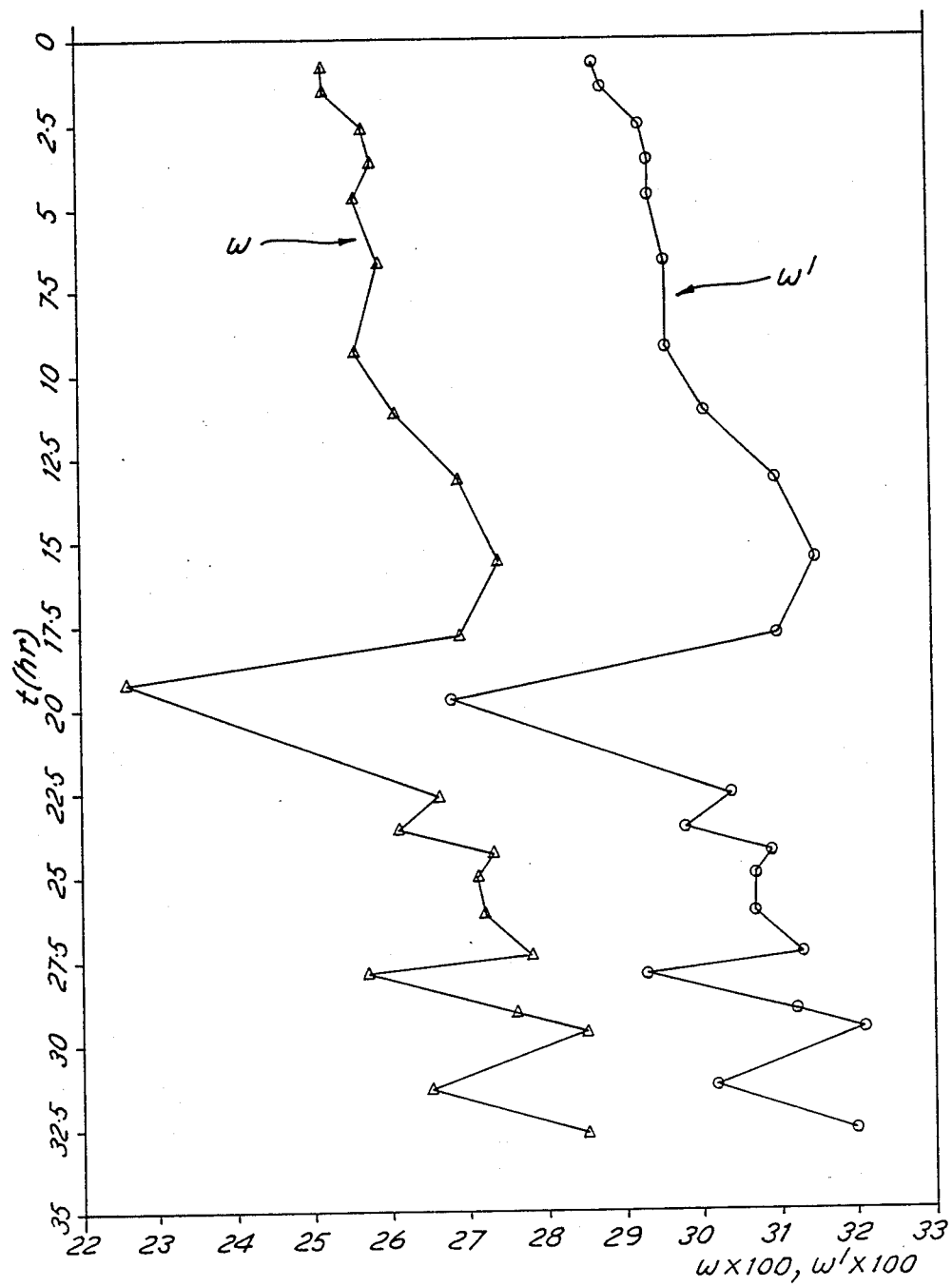
FIG. 4 is a plot of the total dissolved solids versus sample time.

FIG. 4 shows a comparison of w with the uncorrected value w' where the effect of $M_e$ has been ignored, ie, $$w' = \frac{M_m - M_l}{M_m} \quad [7]$$

The maximum difference between w and w' is 4.2 weight percent while the average difference is 3.5 weight percent.

According to one aspect of the invention, the solids removal by the solids control equipment is determined. At the surface, the return and active mud sampling points are separated by the solids control equipment 42. The time lag between the two sampling points is $V_A/Q$ where $V_A$ is the volume of mud in the active tank and Q is the mud flow rate. For this drilled section $V_A$ is approximately 6365 liters and the average flow rate Q is 3090 l/min, and thus the surface time lag is about 20 minutes. A comparison between the values of w in the return flow and active tank mud samples at sample time t (hr) and t+0.3 (hr), respectively, gives the weight percent removal by the solids control equipment. Between t=1 hr and t=16 hr, and t=23 hr and 5=33 hr, the solids content of the active tank mud samples is a constant 0.5% lower than that in the return mud samples. The reduction in w on passing through the solids control equipment is therefore 0.5% which represents a removal of only 2% of the total solids content.

The rate of removal of solids from the mud is given by $$\frac{dM_s}{dt} = Q\Delta w d_m, \qquad [8]$$

where $\Delta w$ is the decrease in solids content and $d_m$ is the mud density. For $\Delta w=0.005$, $d_m=1180$ kgm$^{-3}$ and Q=154 m$^3$/hr (3090 l/min), the rate of solids removal is about 900 kg/hr.

The largely constant separation between the active tank and the return mud solids content logs (FIG. 2) means that the rate of increase of w in the return mud is equal to that of the mud in the active tank. The solids content of the mud system as a whole is therefore increasing and not maintained at a constant value by the solids control equipment. For example, between t=8 hr and t=16 hr, the solids content of the whole mud system increased at a rate of 0.4 weight percent per hour. The rate of solids addition is calculated from $$\frac{dM_s}{dt} = V_t d_m \frac{dw}{dt}, \qquad [9]$$

where $V_t$ is the total volume of mud. With $V_t=212$ m$^3$ (255,000 l) equation [9] predicts a rate of solids addition to the mud of 1000 kg/hr, or a total of 8 tonnes of solid over this time period.

The contribution of any item of solids control equipment (eg, centrifuge) to the removal of solids from the mud system can be measured by taking samples from the mud stream before and after the equipment. The 0.5 weight percent solids removal by the solids control equipment in this particular well can than be broken down into removal by each component of the equipment.

The usual method of combatting the build-up of solids in the mud system is dilution or mud discharge followed by mud replacement. The large decrease in the value of w (FIG. 2) in the active tank mud samples between t=16 hr and t=22 hr is due to dilution of the mud in the active tank. The rather regular pattern of spikes in the active tank solids log following the dilution is the result of intermittent addition of seawater. The main dilution is complete by t=22 hr with the result that the active tank solids content has been reduced from 27.8% to 26.6%. At t=27 hr, some 11 hours after the dilution was instigated, the solids content is back to the pre-dilution value.

The return mud solids log (FIG. 2) shows the effect of dilution in the active tank although a markedly lesser extent. A lag can be seen between the onset of the reduction in w in the active tank and the return mud samples. A comparison between the value of w in the two logs prior to dilution yields a round trip time $t_r$ for the mud of 1.2 hr. The calculated value, obtained from $$t_r = \frac{V_t}{Q}, \qquad [10]$$

is 1.4 hr which is reasonably close to that estimated from the lag in w. Whenever the round trip time has to be measured, the method described in the UK copending patent application No. 8705503 could be used. The value of w in the return mud has been reduced from 29.2% to 27.4%, although by t=24 hr the solids content is increasing at a rate of 0.1.

According to one aspect of the invention, a correlation between the mud solids content and the drilled lithology is made. The description of solids removal in the preceding section emphasized the comparison between the return and active tank mud samples at the surface where the difference between the solids content is largely a result of solids removal by the solids control equipment. The other comparison which can be made is between the active tank and return mud samples (or generally speaking between the mud flowing in the borehole and the mud flowing out of the borehole), where the difference is due to the mud retaining drilled solids which are not removed by the shale shaker, ie, fine solids. The occurrence of fine drilled solids in the mud, as measured by an increase in w, is related to lithology, particularly to dispersing shales which are usually characterised by a high montmorillonite content. The invention is therefore a powerful method for monitoring the stability of the borehole. For example, if the formation being drilled is highly dispersive, the cuttings will dissolve, at least partly, into the mud and this will increase the value of w.

The return mud solids content log (FIG. 2) contains six sharp increases in w of which at least five can be related to the accurately known drilled lithology. The first peak (t=1.7 hr) lies outside the range of the accurately known lithology, although it occurs in an identifiable marl section 54. The second and third peaks occur at the same drilled depth since drilling stopped although the mud was continually circulated. These two peaks occur at time t=7.7 hr and 7=8.9 hr and correspond to a thin (about 3 meters), highly conducting bed in an otherwise uniform limestone section 56. The conductivity of the thin bed is about 2000 mS/m compared to an almost constant value of 300 mS/m for the limestone. This thin bed is a characteristic of the whole field and is used as a marker in each well. The increase in w is due to the almost complete dispersion of cuttings from the thin bed, which is probably a thin bentonite stringer.

The fourth peak, which occurs in the first shale formation 58 at t=16.3 hr, corresponds to a second sharp rise in electrical conductivity from an average value of 800 mS/m to a peak value of 2000 mS/m. This thin bed is also likely to be a stringer of a high montmorillonite content shale. The rise in w at t=18 hr, which constitutes the fifth peak, corresponds to the entry into the second shale section. The second shale is known to contain about 45% montmorillonite and in previous wells gave rise to considerable wellbore stability problems. Dilution of the mud system was made prior to entry into this highly dispersing problem shale, and continual dilution of the active tank mud (spiking in active tank mud solids log) was made to minimise the build-up of drilled solids. The increase in w at 5=18 hr has caught the top of the second shale before the effect of the dilution of the active tank mud is seen in the return mud flow.

The sixth peak, occurring between t=29.6 hr and t=29.9 hr in the third shale 62, also corresponds with a high conductivity thin bed. The electrical conductivity of the thin bed rises from a uniform value of 400 mS/m in the surrounding shale to 1000 mS/m. The gamma ray log shows a sharp spike at this point. The last thin bed is the only feature in this drilled section to show any sudden change in the gamma ray log; the thin bed probably corresponds to an organic-rich high montmorillonite content shale stringer.

The spikes in the return mud solids content log can be correlated with the thin highly conducting beds found by wireline logs. The sample time at which the peak occurs can be converted into drilled depth by a knowledge of the drilled depth as a function of time and the annulus lag time. The estimated depth of the thin beds from the solids content log is within 5 meters of the depth found from wireline logs. The first peak (t=1.7 hr) is predicted to be a thin bentonite bed which occurs at some 51 meters above the E-Log marker.

We claim:

1. A method of monitoring the drilling operations by analyzing the circulating drilling mud, characterized by sampling periodically the mud at the surface, after elimination of the cuttings, and analyzing the samples to determine the successive values as a function of time or depth of a parameter representative of the weight of fine solids present in the mud.

2. The method according to claim 1, further comprising the steps of: determining the weight $M_l$ of the liquid phase and the weight $M_e$ of the electrolyte dissolved in the liquid phase present in a known weight $M_m$ of mud and by determining the weight $M_s$ of the fine solids by the expression:

$$M_s = M_m - M_l - M_e.$$

3. The method according to claim 2, further comprising the step of: determining for each sample the ratio $M_s/M_m$ which represents the fractional weight solids content w.

4. The method according to claim 2 further comprising the step of: drying to constant weight a given weight of mud so as to determine $M_l$.

5. The method according to claim 1 further comprising the step of: determining the weight $M_e$ of electrolyte by chemical analysis of the mud filtrate using an ion chromatography system.

6. The method according to claim 1 further comprising the step of: observing the evolution of the successive values of the parameter so as to monitor the build-up of the fine solids present in the mud.

7. The method according to claim 1 further comprising the step of: sampling the drilling mud flowing in the wellbore and observing the evolution of the successive values of the parameter so as to monitor the dilution of the mud.

8. The method according to claim 1 further comprising the step of: sampling the drilling mud flowing in and out of the borehole at two separate locations where the drilled cuttings have been eliminated from the mud, determining the successive values as a function of time or depth of said parameter representative of the weight solids content of the mud, so as to obtain two series of values related to the mud flowing in and out of the borehole and comparing the two series of values.

9. The method of claim 8, further including the steps of determining the time lag for the mud to travel from one of the said locations to the other, shifting one of the series of values with respect to the other by said time lag or by the depth difference corresponding to said time lag and comparing the two series of values.

10. The method according to claim 8 or 9 in which the drilling mud passes through an apparatus comprising means for removing the drilled cuttings and equipment for controlling the solids, further including the step of comparing the series of values corresponding to samples taken right after the drilled cuttings-removal means with the series of values corresponding to samples taken after the solids control equipment so as to determine the efficiency of said equipment which excludes the cuttings-removal means.

11. The method according to claim 8 further including the step of: comparing the series of values corresponding to the mud going in the wellbore with the series of values corresponding to the mud returning from the wellbore, so as to correlate the result of said comparison with the drilled lithology.

* * * * *